(12) United States Patent
Donitzky et al.

(10) Patent No.: US 8,715,272 B2
(45) Date of Patent: *May 6, 2014

(54) DEVICE AND PROCESS FOR MACHINING THE HUMAN EYE USING LASER TECHNOLOGY

(71) Applicant: WaveLight GmbH, Erlangen (DE)

(72) Inventors: Christof Donitzky, Eckental (DE); Jörg Klenke, Nürnberg (DE); Christian Wüllner, Möhrendorf (DE)

( * ) Notice: Subject to any disclaimer, the term of this patent is extended or adjusted under 35 U.S.C. 154(b) by 61 days.

This patent is subject to a terminal disclaimer.

(21) Appl. No.: 13/865,487

(22) Filed: Apr. 18, 2013

(65) Prior Publication Data

US 2013/0274723 A1    Oct. 17, 2013

Related U.S. Application Data

(63) Continuation of application No. 12/894,364, filed on Sep. 30, 2010, now Pat. No. 8,449,534.

(51) Int. Cl.
*A61F 9/01* (2006.01)
(52) U.S. Cl.
USPC ............................................................. 606/5
(58) Field of Classification Search
USPC ............................................................. 606/5
See application file for complete search history.

(56) References Cited

U.S. PATENT DOCUMENTS

2008/0319428 A1    12/2008    Wiechmann et al.

FOREIGN PATENT DOCUMENTS

| DE | 102009009382 A1 | 8/2010 |
| WO | 94/09849 A1 | 5/1994 |

*Primary Examiner* — Bill Thompson
*Assistant Examiner* — John R Downey

(57) ABSTRACT

A device for machining the human cornea with focused laser radiation includes controllable components for setting the location of the radiation focus, a control computer for controlling these components, and also a control program for the control computer. The control program contains instructions that have been designed to bring about, upon execution by the control computer, the generation of incisions in the cornea in accordance with a predetermined incision figure, the incision figure defining a corneal bed, a flap situated on the bed and also at least one tissue strip situated in the region of the peripheral edge of the flap between the bed and the flap and extending along the edge of the flap. After the flap has been folded away, the tissue strip has to be removed and enables a creaseless post-ablative close fitting of the folded-back flap against the surface of the bed. In this manner, microstriae which may impair the visual capacity can be avoided.

11 Claims, 2 Drawing Sheets

DEVICE AND PROCESS FOR MACHINING THE HUMAN EYE USING LASER TECHNOLOGY

The invention is concerned with the generation of incisions in the human cornea by means of focused and customarily pulsed laser radiation. In particular, the invention is concerned with the implementation of a LASIK treatment and with the preparation of a LASIK flap by means of such laser radiation.

BACKGROUND OF THE INVENTION

A frequently employed technique for eliminating visual defects of the human eye—such as, for example, short-sightedness or long-sightedness or/and astigmatism—is so-called LASIK. LASIK stands for laser in-situ keratomileusis and designates a technique in which firstly a small disc (lamella) is cut free on the surface of the cornea, said disc being folded aside in order to expose the underlying tissue regions of the cornea. These exposed tissue regions are then treated in ablating manner by means of focused UV laser radiation, i.e. corneal material is resected in accordance with an ablation profile ascertained individually for the patient.

The surface disc of the cornea which is cut free is usually designated in specialist circles as a flap; it is not detached completely from the remaining cornea but is still connected to the remaining corneal tissue in a hinge region, commonly designated in specialist circles as a hinge. This enables a simple folding-away of the flap and, above all, a simple folding-back of the flap after the ablation. On account of the resection of material, after the flap has been folded back a changed shape of the anterior surface of the cornea appears. This results in a different refractive behaviour of the cornea and consequently of the overall system constituted by the eye. By suitable establishment of the ablation profile, it can be ensured that the visual defect is at least distinctly attenuated and at best is even almost completely eliminated.

Various procedures are known in the state of the art for the preparation of the flap. One procedure utilises a mechanical microkeratome, i.e. a microsurgical plane which cuts into the cornea with a cutting blade which is ordinarily driven in oscillating manner. Another procedure, which will be considered in more detail within the scope of the invention, utilises focused ultra-short-pulse laser radiation for the purpose of preparing the flap. Ordinarily, laser radiation with pulse durations within the femtosecond range, but at any rate within the low picosecond range, is employed in this case. For the placement of corneal incisions, the laser radiation that is used for this purpose must have a wavelength above about 300 nm, in order to enable a coupling of the radiant energy deep into the corneal tissue. LASIK treatments in which the flap is prepared by means of such ultra-short-pulse laser radiation are often designated as fs LASIK.

For the generation of incisions by means of focused laser radiation in transparent material (transparent to the laser radiation), the so-called laser-induced optical breakthrough is utilised by way of physical effect. This results in a photodisruption of the irradiated tissue in the region of the focus. By setting a plurality of such photodisruptions alongside one another, two-dimensional and three-dimensional incision figures can be realised in the cornea (and also in other tissue parts of the eye, which, however, will not be considered further here). The radiation parameters of the laser radiation may have been set in such a way that each individual laser pulse results in a photodisruption. Equally, it is conceivable to set the radiation parameters in such a way that a photodisruption occurs only after beaming several (at least two) laser pulses onto substantially the same point.

Especially in the case of the correction of a case of myopia (short-sightedness) by a LASIK treatment, the problem arises that after the ablation the flap can no longer fit optimally into the wound area (corneal bed). This is because for the purpose of correcting a case of myopia the most intensive resection of material commonly takes place in the centre of the ablatively machined optical zone. As a result of this, the radius of curvature of the optical zone decreases in comparison with the state before the ablation. This is accompanied by a diminution of the arc length of the optical zone measured along the surface. If the flap is now folded back onto the corneal bed, it may be that it does not fit perfectly snugly into the bed but that creases arise in the flap. This phenomenon, also designated as striae, may give rise to unpleasant impairments of the vision of the patient. For the purpose of eliminating the complications as a consequence of striae of the flap, one idea may be, for example, to heat the flap after folding it back onto the bed and to smooth it out. However, this constitutes an additional burdening of the patient by virtue of a further treatment step.

BRIEF SUMMARY OF THE INVENTION

An object of the invention is to make LASIK operations on the human eye, in particular those for eliminating a case of myopia, agreeable for the patient, with visual impairments that are as slight as possible.

With a view to achieving this object, according to one aspect a device is provided for machining the human cornea with focused laser radiation, the device including controllable components for setting the location of the radiation focus, a control computer for controlling these components, and a control program for the control computer. The control program contains instructions that are designed to bring about, upon execution by the control computer, the generation of incisions in the cornea in accordance with a predetermined incision figure, the incision figure defining a corneal bed, a flap situated on the bed and also at least one corneal tissue strip situated in the region of the peripheral edge of the flap between the bed and the flap and extending along the edge of the flap.

The invention is based on the recognition that by targeted shortening of the flap the formation of striae can be avoided better, so that subsequent elaborate smoothing measures in respect of the cornea can be dispensed with. The shortening of the flap is expediently such that, after the ablative treatment, the flap fits exactly into the corneal (stromal) bed and does not form creases or forms at least only insignificant creases. For the purpose of shortening the flap, on the peripheral edge of the flap at least one tissue strip is cut free which is removed after the flap has been folded upwards. The incision figure expediently provides for a complete separation of this tissue strip from the flap and from the surrounding corneal bed. Depending on whether and to what extent after placement of the incisions the tissue strip is still linked with adjacent tissue via narrow tissue bridges between consecutive photodisruptions, it may be that in the course of folding the flap upwards the tissue strip either follows the flap or remains situated in the bed. For the operating surgeon it is, in any case, equally easy to remove the tissue strip, by pulling it away from the bed or from the flap, as the case may be.

The tissue strip may extend substantially over the entire peripheral length of the edge of the flap—that is to say, substantially over the entire length of the edge from one end of the hinge to the other. Alternatively, the tissue strip may extend only over a part of the peripheral length of the edge of the flap, it even being conceivable that the incision figure defines a plurality of at least two tissue strips which extend along different peripheral regions of the edge of the flap. The number and peripheral length of the tissue strips depend, above all, on the ablation profile, which is frequently not rotationally symmetrical but—for example, when an astigmatism is present—may be asymmetrical in the peripheral direction. Such asymmetries may then also be reflected in a variable cross-section of the tissue strip in the peripheral direction of the edge of the flap.

The tissue strip may be situated completely beneath the corneal surface, so that a shortening of the flap takes place only beneath the anterior surface of the cornea. It is, of course, equally conceivable that the tissue strip reaches as far as the anterior surface of the cornea and possesses there a non-vanishing, finite width. In this case a—slight—shortening of the flap takes place also on the anterior surface of the cornea. This may be necessary, depending on the intensity of the resection of material in the course of the later ablation.

In view of the arc length of the optical zone which is diminished post-ablatively in the course of treatment of a case of myopia, it is expedient if the cross-section of the tissue strip has an increasing width when viewed in the direction from the anterior surface of the cornea towards deeper regions of the cornea. The cross-section of the tissue strip may, for example, be approximately wedge-shaped.

For the purpose of preparing the flap and the tissue strip, the incisions may include a first incision, defining the underside of the flap, situated completely deep within the cornea and preferentially extending parallel to the anterior surface of the cornea, and also two second incisions, spaced from one another, in particular running into the first incision in angled manner and delimiting the tissue strip between themselves and the first incision, of which at least one is conducted out to the anterior surface of the cornea. In this case the two second incisions may run into one another beneath the anterior surface of the cornea. If the tissue strip is to reach as far as the anterior surface of the cornea, however, the two second incisions may run into one another directly on the anterior surface of the cornea or, spaced from one another, may have been conducted out as far as the anterior surface of the cornea, without intersecting one another.

According to a preferred embodiment, the control computer may have access to ablation data that are representative of a corneal ablation profile, the control computer having been set up to determine, on the basis of the ablation data, the incision figure, in particular the cross-section of the tissue strip, in a manner depending on the peripheral location of the edge of the flap. By the ablation data being made available in such a manner to the laser device making the LASIK incisions, the tissue strip to be removed can be optimally established in terms of shape and size. It will be understood, however, that, instead of being established on the basis of patient-specific ablation data, the cross-section of the tissue strip—that is to say, its shape and its size—may be established on the basis of empirical data or on the basis of defined theoretical models.

A process for machining a human eye includes, according to a further aspect, the following steps:
  generating incisions in the cornea of the eye by means of first focused laser radiation in accordance with a predetermined incision figure, the incision figure defining a corneal bed, a flap situated on the bed and also at least one corneal tissue strip situated in the region of the peripheral edge of the flap between the bed and the flap and extending along the edge of the flap,
  folding the flap upwards,
  removing the at least one tissue strip,
  ablating the exposed bed tissue by means of second focused laser radiation in accordance with an ablation profile,
  folding the flap back.

The process may further include the step of determination of the incision figure on the basis of the ablation profile. The determination of the incision figure may include the ascertaining of a length-difference, existing after the ablation in comparison with before the ablation, of at least one line segment measured across at least one part of the bed surface and also an establishing of the cross-section of the tissue strip on the basis of the ascertained length-difference. The line segment measured across the bed surface is, for example, one which passes through the centre of the ablatively treated optical zone from one edge of the zone to the opposite edge. To this extent, the length of this line segment corresponds to the arc length of the optical zone measured across the centre. To the extent that a rotationally asymmetrical resection of material is to be effected within the scope of the ablation, it is advisable to ascertain the difference in arc length (i.e. before as opposed to after the ablation) for a plurality of different angular positions, for example by utilising topographical data pertaining to the anterior surface of the cornea or to the bed surface, in order in this way to be able to adapt the geometry of the tissue strip individually. This enables an optimal determination of the progression of the cross-section of the tissue strip in the peripheral direction and hence an optimal adaptation of the cross-section of the strip to the circumstances of the individual patient.

BRIEF DESCRIPTION OF THE DRAWINGS

The invention will be elucidated further in the following on the basis of the appended drawings. Represented are.

DETAILED DISCUSSION OF PREFERRED EMBODIMENTS

Figure 1:
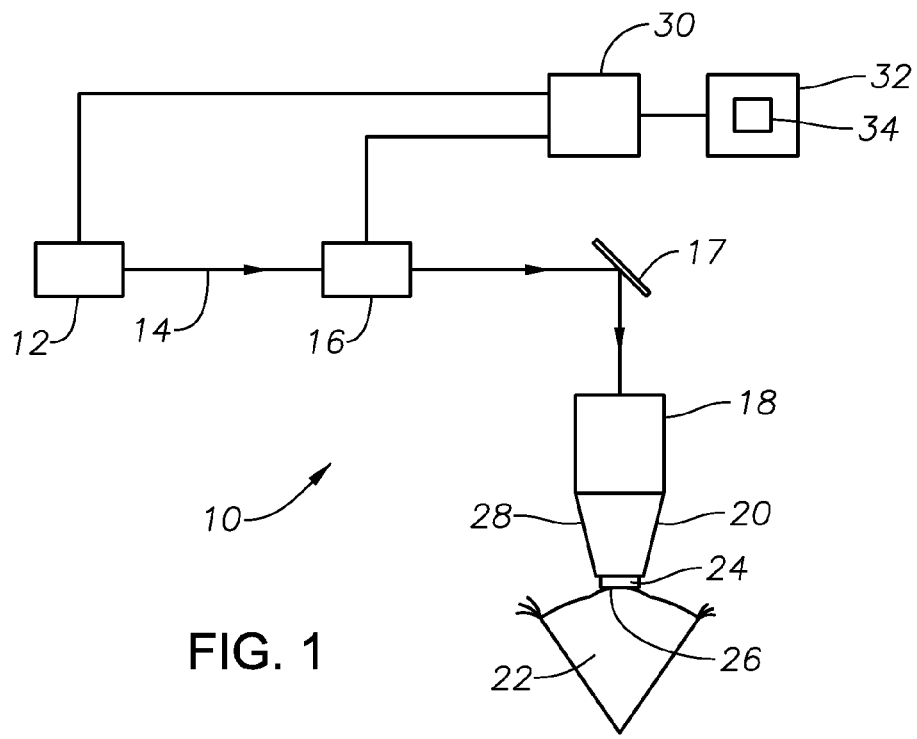
FIG. 1: in schematic block representation, an embodiment of a laser device for placing intracorneal incisions.

The laser device shown in FIG. 1, generally denoted by 10, includes a laser-source 12 which generates a laser beam 14 with pulse durations within the femtosecond range. In the beam path of the laser beam 14 a number of components are arranged, inter alia a scan module 16 indicated here schematically as a unified functional block, an immovable deviating mirror 17 and also a focusing objective 18. The scan module 16 serves for transverse and longitudinal control of the location of the focal point of the laser beam 14. 'Transverse' designates here a direction at right angles to the direction of propagation of the laser beam 14; 'longitudinal' means along the direction of beam propagation. For the purpose of transverse deflection of the laser beam 14, the scan module 16 may, for example, include a pair of galavanometrically actuated scanner mirrors which are capable of being tilted about mutually perpendicular axes. Alternatively, for example, a transverse deflection by means of an electro-optical crystal is conceivable.

For the longitudinal control of the focal position, the scan module 16 may, for example, contain a longitudinally adjustable lens or a lens of variable refractive power or a deformable mirror, with which the divergence of the laser beam 14 and consequently the longitudinal position of the beam focus can be influenced.

It will be understood that the components of the scan module 16 serving for the transverse and the longitudinal setting of the location of the focus may be distributed along the beam path of the laser beam 14 and, in particular, may be accommodated in different modular units. For example, the function of the longitudinal focus control may be fulfilled by a lens arranged in a beam expander (e.g. Galilean telescope), whereas the components serving for the transverse focus control may be accommodated in a separate modular unit between the beam expander and the focusing objective 18. The representation of the scan module 16 as a unified functional block in FIG. 1 serves merely for better clarity of layout.

The focusing objective 18 is preferably an f-theta objective and is preferentially separably coupled on its beam-emergence side with a patient adapter 20 which forms an abutment interface for the cornea of an eye 22 to be treated. For this purpose the patient adapter 20 exhibits a contact element 24 which is transparent to the laser radiation and which on its underside facing towards the eye exhibits an abutment face (contact face) 26 for the cornea. The abutment face 26 is constructed, in the exemplary case that is shown, as a plane face and serves for leveling the cornea, by the contact element 24 being pressed against the eye 22 with appropriate pressure or by the cornea being aspirated onto the contact face 26 by reduced pressure. The contact element 24 (in the case of plane-parallel construction, ordinarily designated as an applanation plate) is attached at the narrow end of a spacer cone 28. The connection between the contact element 24 and the spacer cone 28 may be inseparable, for example by virtue of adhesion bonding; alternatively it may be separable, for instance by virtue of a screw joint. The spacer cone 28 possesses at its wide end, in a manner not represented in any detail, suitable coupling structures for longitudinal and transverse, positionally stable coupling to the focusing objective 18.

The laser-source 12 and the scan module 16 are controlled by a control computer 30 which operates in accordance with a control program 34 stored in a memory 32. The control program 34 contains instructions (program code) that bring about, upon execution by the control computer 30, such a control of the location of the beam focus of the laser beam 14 that a LASIK flap arises in the cornea of the eye 22 bearing against the contact element 24. Before considering particulars of this flap, let reference briefly be made to FIG. 2, where for the eye 22 a conventional corneal flap 36 is shown schematically which is separated from the remaining corneal tissue by a bed incision 38 and a marginal incision 40 and is situated snugly in the stromal bed delimited by the incisions 38, 40. This bed is denoted here by 42.

Figure 2:
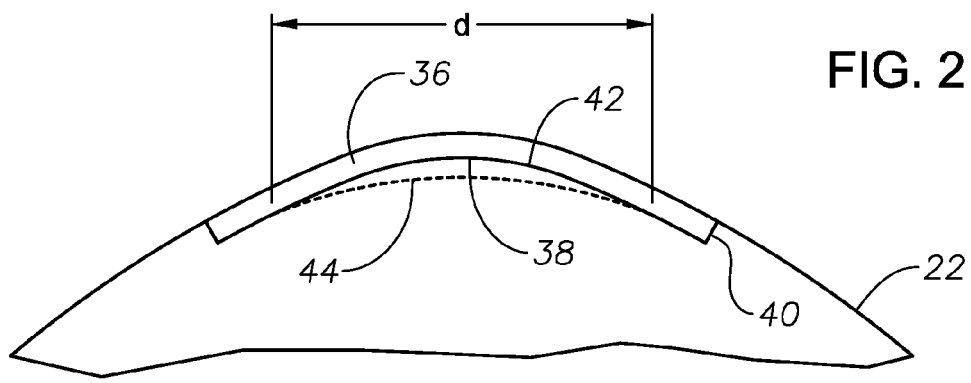
FIG. 2: schematically, the conditions before and after the ablation in the case of a LASIK treatment for correcting a case of myopia.

In FIG. 2 let the case be assumed that the bed 42 is treated in ablating manner with suitable UV laser radiation in an optical zone with diameter d. It will be understood that for this purpose the flap 36 previously has to be folded aside, in order to expose the optical zone to be machined. The ablation is to serve for the purpose of correcting a case of myopia, i.e. the resection of material is greatest in the centre of the optical zone and decreases towards the edges of the optical zone. Post-ablatively, therefore, a surface of the bed 42 arises such as is indicated in exemplary form in dotted manner at 44. It is readily apparent that the line segment measured across the centre of the optical zone on the surface of the bed from edge to edge is shorter post-ablatively than pre-ablatively. This holds for the edge-to-edge line segment of the ablated optical zone, just as for the edge-to-edge line segment of the bed as a whole. To the extent that the resection of material is rotationally symmetrical, the shortening of the arc length of the bed surface in all meridional directions is at least approximately the same. In the case of a more complex ablation profile, which demands different intensities of the resection in different meridional directions, the difference in arc length of the bed surface may vary correspondingly between pre-ablative and post-ablative states.

Regardless of this, the shortening of the arc length of the bed surface has the consequence that after the ablation the flap 36 cannot fit snugly into the—now lowered—bed 42: because the underside of the flap in the region of the optical zone has a greater arc length than the ablated bed surface, upon being folded back the flap 36 does not bear with its full area against the bed surface. Instead of this, it forms relatively small creases (microstriae). Without subsequent supplementary measures these microstriae remain, and they impair the visual acuity considerably in some cases.

It will be understood that the observations made in connection with FIG. 2 relate to the non-applaned state of the eye—that is to say, to a state in which the eye 22 is no longer bearing against the contact plate 24 of the laser device shown in FIG. 1.

In order to obtain an improved post-ablative close fitting of the LASIK flap against the stromal bed, the incision figure represented by the control program 34 provides for a marginal shortening of the flap, by an approximately wedge-shaped tissue strip being separated there from the edge of the flap. In this regard, reference will now be made to FIG. 3. Even though the flap shown therein is a flap that has been shortened in accordance with the invention, for reasons of clarity of layout nevertheless in FIG. 3 and in the following Figures the same reference symbols will be used as in FIG. 2.

Figure 3:
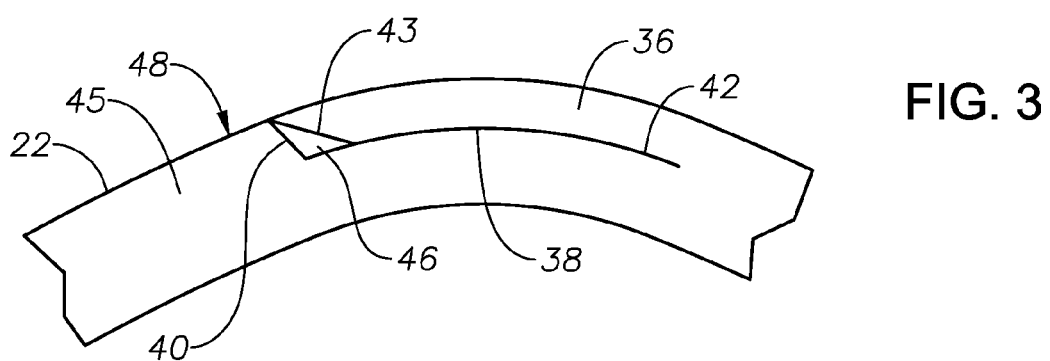
FIG. 3: schematically, a LASIK flap that has been shortened at the edge in the shape of a wedge.

The incision figure shown in FIG. 3 includes, in addition to the bed incision 38 and the marginal incision 40, a wedge incision 43 which proceeds radially (relative to an imaginary centre, not represented in any detail, of the cornea, denoted by 45, of the eye 22) at least very largely within the marginal incision 40 in the peripheral direction of the edge of the flap and, together with the marginal incision 40 and the bed incision 38, delimits a tissue strip 46 which is approximately wedge-shaped in cross-section and which can be taken out after the raising and folding-away of the flap 36. In the exemplary case that is shown, the bed incision 38 proceeds at a substantially uniform depth of the cornea 45 parallel to the anterior surface of the cornea, denoted by 48. The marginal incision 40 and also the wedge incision 43 proceed in angled manner relative to the bed incision 38 in the direction towards the anterior surface 48 of the cornea. The radial spacing between the marginal incision 40 and the wedge incision 43 is greatest in the region of the bed incision 38; upon advancing in the direction towards the anterior surface 48 of the cornea, the marginal incision 40 and the wedge incision 43 approach one another.

The size of the tissue wedge formed by the strip 46 depends on the post-ablative diminution of the arc length of the bed surface in the meridional direction in question. Furthermore, the size depends on whether this reduction in arc length can be balanced out by a single tissue wedge or by two tissue wedges situated in diametrically opposed marginal regions of the flap.

In those marginal regions of the flap which are situated opposite the hinge, the entire difference in arc length in the direction in question has to be compensated by a single tissue wedge. In the remaining meridional directions the difference in arc length can be compensated by two tissue wedges at marginal points of the flap situated opposite one another. Accordingly, the size and shape (or generally, the cross-section) of the tissue strip 46 may vary upon progressing in the peripheral direction of the edge of the flap. In particular, in those marginal regions which are situated opposite the hinge the tissue strip 46 may have a larger cross-section than in the remaining peripheral regions.

Figure 7:
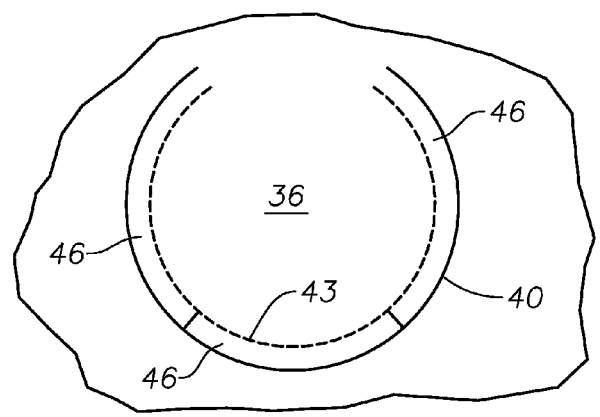
FIG. 7: anterior view of tissue strips formed during generation of a shortened LASIK flap.

Depending upon the ablation profile, the tissue strip 46 may extend over the entire periphery of the edge of the flap. It is also conceivable that the tissue strip 46 extends only along a segment of the edge of the flap. It is even conceivable to generate along the edge of the flap several tissue strips 46 spaced from one another in the peripheral direction, as shown in FIG. 7.

Even though in FIG. 3 and in the following Figures the marginal incision 40 and the wedge incision 43 are each represented as rectilinear incisions in cross-section, it will be understood that this is by no means imperative. In particular, for the wedge incision 43 an incision course that is not straight may also readily be chosen.

Figure 4:
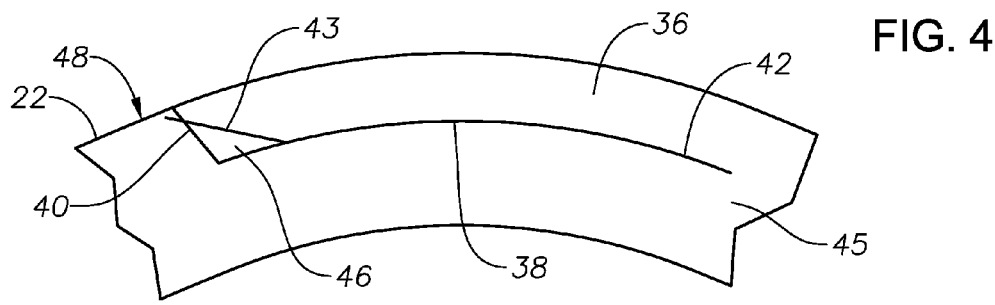
FIGS. 4-6: various variants of the placing of an incision for the purpose of generating a shortened LASIK flap.
Figure 5:
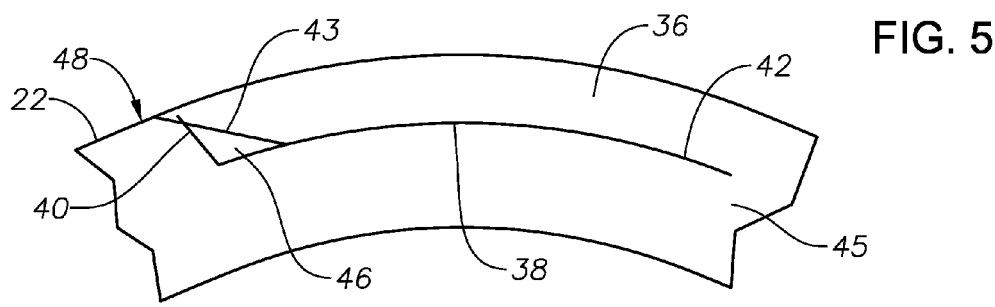
Figure 6:
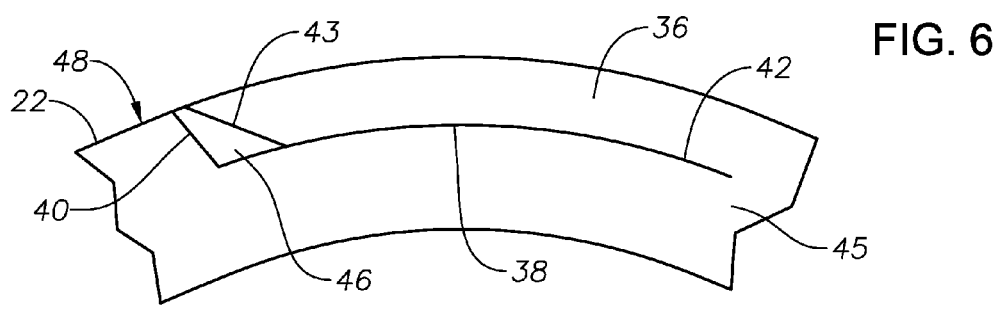

In the exemplary case shown in FIG. 3 the marginal incision 40 and the wedge incision 43 impinge on one another substantially directly on the anterior surface 48 of the cornea. FIGS. 4 to 6 show various modifications for the relative course of the marginal incision 40 and of the wedge incision 43.

In FIG. 4 the marginal incision 40 and also the wedge incision 43 intersect beneath the anterior surface 48 of the cornea, the wedge incision 43 terminating at a spacing from the anterior surface 48 of the cornea, and the marginal incision 40 being continuous as far as the anterior surface 48 of the cornea.

In the variant shown in FIG. 5 the marginal incision 40 and the wedge incision 43 intersect likewise beneath the anterior surface 48 of the cornea, whereby, however, in this case the marginal incision 40 terminates at a spacing before the anterior surface 48 of the cornea and, instead, the wedge incision 43 is continuous as far as the anterior surface 48 of the cornea.

The modification according to FIG. 6 shows a case in which both the marginal incision 40 and the wedge incision 43 are continuous as far as the anterior surface 48 of the cornea and run into the anterior surface 48 of the cornea at a spacing from one another, without, however, intersecting one another.

By the flap being shortened at its edge in the manner elucidated above, preferentially in the shape of a wedge, it is possible to modify it in such a way that it can be inserted exactly into the post-ablative stromal bed. As elucidated, the shortening may be performed on the entire flap, with the exception of those regions where the hinge is located. The calculation of the cross-section of the tissue strip 46, i.e. generally the calculation of the corneal incision figure, can be carried out by taking into account the size of the ablatively treated optical zone, the refractive powers of the cornea before and after the ablation, and also the asphericities of the anterior surface of the cornea. A possible foundation of the calculation is given by the mathematical formulae reproduced below.

$$P = \frac{n-1}{R} \to R_1 = \frac{n-1}{P_{preop}}; \quad [1]$$

$$R_2 = \frac{n-1}{P_{postop}}; \quad R_2 > R_1$$

$$s = \frac{1}{1+Q_1}[R_1^2 - y^2(1+Q_1)]^{1/2} - \frac{1}{1+Q_2}[R_2^2 - y^2(1+Q_2)]^{1/2} + \quad [2]$$

$$\frac{1}{1+Q_2}\left[R_2^2 - \frac{OZ^2}{4}(1+Q_2)\right]^{1/2} - \frac{1}{1+Q_1}\left[R_1^2 - \frac{OZ^2}{4}(1+Q_1)\right]^{1/2}$$

$$b_1 = 2R_1 * \arcsin\left(\frac{OZ}{2R_1}\right)$$

$$b_2 = 2R_2 \arcsin\sqrt{\left(1 - \left(\frac{s(y=0) - R_1 + R_2 + \sqrt{R_1^2 - \frac{OZ^2}{4}}}{R_2}\right)^2\right)}$$

$$\Delta b = b_1 - b_2$$

$P_{preop}$: refractive power of the cornea before the operation (e.g. $P_{preop}$=43 dpt)
$P_{postop}$: desired refractive power of the cornea after the operation
$R_1$: radius of curvature of the optical zone before the ablation
$R_2$: radius of curvature of the optical zone after the ablation
n: refractive index of the cornea (n≈1.377)
$b_1$: arc length of the optical zone before the ablation
$b_2$: arc length of the optical zone after the ablation
OZ: diameter of the optical zone
$Q_1$: asphericity of the anterior surface of the cornea before the ablation (−1<$Q_1$<1))
$Q_2$: asphericity of the anterior surface of the cornea after the ablation (−1<$Q_2$<1))
s: depth of the ablation
y: radial indexed variable (y=0 at the point of maximal ablation, i.e. ablation centre)

With the aid of the above mathematical foundations, for a purely central (rotationally symmetrical) resection of material, taking account of the asphericities of the anterior surface of the cornea, the difference in arc length Δb (post-ablative in comparison with pre-ablative) of the optical zone can be calculated. With knowledge of the difference in arc length, it is readily possible to calculate the cross-section of the tissue strip 46 to be removed. In this connection, as elucidated, it is to be taken into consideration that diametrically relative to the hinge the shortening is to be effected by a single tissue wedge, whereas on the remaining sides the shortening can be apportioned to two tissue wedges.

In purely exemplary manner the following numerical table was ascertained by computation on the assumption of asphericity values $Q_1$=$Q_2$=−0.3 and a size (diameter) of the optical zone of 6.5 mm. This specifies, for different values of short-sightedness to be corrected, the resulting difference in arc length of the optical zone. These numerical values were calculated using the mathematical foundations reproduced above.

| Values [dpt] to be corrected | Difference in arc length [μm] |
| --- | --- |
| 1 | 5 |
| 2 | 10 |
| 3 | 14 |
| 4 | 19 |
| 5 | 23 |
| 6 | 27 |
| 7 | 30 |
| 8 | 34 |

The control computer 30 of the laser device according to FIG. 1 preferentially has access to suitable ablation data that are representative of the resection of material to be realised. The ablation data may, for example, have been stored in the memory 32. In this connection it is conceivable that the memory 32 is accessible also for a control computer of a separate laser device, not represented in any detail, for the later ablating treatment of the eye. The ablation data can be written into the memory 32 by the control computer of this ablation laser device, in which connection the control computer 30 of the cutting laser device shown in FIG. 1 calculates, on the basis of the ablation data, the suitable incision figure for the respective patient.

The invention claimed is:

1. A method for controlling, by a control computer, one or more components that set a location of a radiation focus in a cornea according to an incision figure, the method comprising:
    generating, by the components, a bed incision of the incision figure at a uniform depth of the cornea to create a corneal bed;
    generating, by the components, a wedge incision of the incision figure to create a peripheral edge of a corneal flap disposed anterior to the corneal bed; and
    generating, by the components, a marginal incision of the incision figure, a majority of the marginal incision disposed outwardly from the wedge incision in a radial direction, the bed incision, the wedge incision, and the marginal incision defining at least one separable tissue strip along the edge of the flap, the tissue strip having a radial width perpendicular to the edge of the flap and parallel to the anterior surface of the cornea, the radial width increasing from the most anterior part of the strip towards the most posterior part of the strip.

2. The method of claim 1, wherein generating, by the components, the marginal incision further comprises:
    generating the marginal incision such that the tissue strip extends along the entire edge of the flap.

3. The method of claim 1, wherein generating, by the components, the marginal incision further comprises:
    generating the marginal incision such that the tissue strip extends along only a part of the edge of the flap.

4. The method of claim 1, wherein generating, by the components, the marginal incision further comprises:
    generating the marginal incision such that at least two tissue strips extend along different parts of the edge of the flap.

5. The method of claim 1, wherein generating, by the components, the marginal incision further comprises:
    generating the marginal incision such that the tissue strip is completely beneath the anterior surface of the cornea.

6. The method of claim 1, wherein generating, by the components, the marginal incision and generating, by the components, the wedge incision further comprise:
    generating the marginal incision and the wedge incision such that a cross-section of the tissue strip varies in a peripheral direction along the edge of the flap.

7. The method of claim 1, wherein generating, by the components, the marginal incision and generating, by the components, the wedge incision further comprise:
    generating the marginal incision and the wedge incision such that a cross-section of the tissue strip is wedge-shaped.

8. The method of claim 1, further comprising:
    folding the flap upwards; and
    removing the at least one tissue strip.

9. The method of claim 8, further comprising:
    ablating the exposed corneal bed according to an ablation profile.

10. The method of claim 1, further comprising:
    determining the incision figure in accordance with an ablation profile.

11. The method of claim 1, further comprising:
    ascertaining a shortening of the arc length of the corneal bed in accordance with an ablation profile; and
    determining the incision figure in accordance with the shortening of the arc length.

* * * * *